United States Patent [19]

Grate et al.

[11] Patent Number: 4,629,804

[45] Date of Patent: * Dec. 16, 1986

[54] PROCESS FOR PREPARATION OF URETHANES

[75] Inventors: John H. Grate; David R. Hamm, both of Mountain View, Calif.; Donald H. Valentine, Jr., Ridgefield, Conn.

[73] Assignee: Catalytica Associates, Mountain View, Calif.

[*] Notice: The portion of the term of this patent subsequent to Jul. 15, 2003 has been disclaimed.

[21] Appl. No.: 707,885

[22] Filed: Mar. 4, 1985

Related U.S. Application Data

[63] Continuation-in-part of Ser. No. 532,784, Sep. 16, 1983, Pat. No. 4,600,793, and a continuation-in-part of Ser. No. 532,785, Sep. 16, 1983, Pat. No. 4,603,216.

[51] Int. Cl.$^4$ .............. C07C 125/065; C07C 125/073; C07C 125/077
[52] U.S. Cl. ........................................ 560/24; 560/25; 560/27; 560/28; 560/29; 560/30; 560/115; 560/157; 560/158
[58] Field of Search .................. 560/24, 25, 27, 28, 560/29, 30, 115, 157, 158

[56] References Cited

U.S. PATENT DOCUMENTS 4,474,978  10/1984  Drent et al. ........................ 560/24
4,491,670  1/1985  Bhaduri et al. ..................... 560/24

FOREIGN PATENT DOCUMENTS 57102855  12/1980  Japan .................................. 560/24

Primary Examiner—Bernard Helfin
Attorney, Agent, or Firm—Robert J. Baran; John H. Grate

[57] ABSTRACT

This invention relates to a process for preparing urethanes by reacting a solution of a nitrogen-containing organic compound and a hydroxyl-containing organic compound with carbon monoxide in the presence of a ruthenium catalyst. The selectivity of this process is increased by the use of methanol instead of various other alkanols, e.g. ethanol. Preferably the catalyst is a halide-free ruthenium catalyst, e.g. a ruthenium carbonyl complex.

26 Claims, No Drawings

PROCESS FOR PREPARATION OF URETHANES

CROSS REFERENCE TO RELATED PATENT APPLICATIONS

The patent application is a continuation-in-part of U.S. patent application Ser. Nos. 532,784 and 532,785, both entitled "Process for the Preparation of Urethanes", and filed on Sept. 16, 1983, in the names of Grate, Hamm and Valentine and now U.S. Pat. Nos. 4,600,793 and 4,603,216 respectively. Both of these patent applications are hereby incorporated by reference in their entirety.

BACKGROUND OF THE INVENTION

1. Field of the Invention

This invention relates to a process for preparing urethanes by reacting a solution of a nitrogen-containing organic compound and a hydroxyl-containing organic compound with carbon monoxide in the presence of a ruthenium catalyst.

2. Description of the Art

Isocyanates such as toluene diisocyanate (TDI) and 4,4-diisocyanato diphenyl methane (MDI) are used commercially in the preparation of urethane polymers. The present commercial technology for the preparation of these isocyanates utilizes phosgene, which is costly, toxic, corrosive, and difficult to handle. It is thus understandable that a great deal of recent research has been directed toward different methods for preparing isocyanates, especially TDI and MDI.

Various patents have disclosed methods for carbonylating nitrogen-containing organic compounds, e.g. nitro compounds, amines, azo- and azoxy compounds to either isocyanates or urethanes in the presence of a platinum group metal-containing catalyst; usually a palladium or rhodium-containing catalyst, and most often a palladium halide-containing catalyst. (The urethanes can be decomposed to yield the corresponding isocyanates.) Generally, a cocatalyst (promoter) or a coreactant has been utilized in combination with the aforementioned platinum group metal-containing catalysts; Lewis acids, Lewis bases, oxidizing agents, reducing agents, etc. have been used as cocatalysts or coreactants in the platinum group metal-catalyzed carbonylation of nitrogen-containing organic compounds. It is important to note that the vast majority of the research on the carbonylation of nitrogen-containing organic compounds has been directed to catalysis by rhodium or palladium-containing catalysts; especially palladium halide-containing catalysts.

In references which teach the use of palladium catalysts, for the above reaction, generally the alcohol of choice is ethanol. See, for example, U.S. Pat. Nos. 3,531,512; 3,993,685; 4,134,880; 4,186,269; 4,219,661; 4,262,130; 4,297,501 4,304,922 and 4,339,592. In U.S. Pat. No. 4,297,501, ethanol is demonstrated to provide improved selectivity to the urethane as compared to methanol. In U.S. Pat. No. 4,134,880, methanol, ethanol and various higher alcohols are demonstrated to give similar selectivities to the urethane.

European Patent Application No. 86,281 teaches the use of methanol and a catalyst comprising palladium and a specific ligand having two moieties selected from the group consisting of nitrogen, phosphorus, arsenic and antimony. The novelty of this invention is predicated on the use of the specific ligand disclosed in the patent application in combination with palladium as a catalyst.

In the references which teach the use of rhodium catalysts for the above reaction, the use of methanol and other alcohols in the conversion of the above nitrogen-containing compounds to urethanes, in the presence of carbon monoxide, is disclosed. Again, generally the alcohol of choice is ethanol. See for example, U.S. Pat. Nos. 3,993,685; 4,134,880; 4,186,269; and 4,304,922. In U.S. Pat. No. 3,338,956, methanol is stated as a preferred alcohol, but no reason for preference is given in the disclosed, rhodium halide catalyzed process. (There is no demonstration, by example, of ethanol, therefore there is no basis for the preference of methanol, especially in view of the patents that teach ethanol is preferred). Similarly, methanol is allegedly preferred in the urethane process disclosed in U.S. Pat. No. 3,448,140, but variations in selectivity appears to be dependent on the catalyst metal rather than the alcohol. (This reference discloses Group VIII metals demonstrate varying efficiencies for catalyzing the conversion of a nitrogen-containing compound to urethane in the presence of an alcohol and carbon monoxide.) See also U.S. Pat. Nos. 3,454,620 and 3,467,694, wherein methanol is an alcohol demonstrated as useful in the above process but the effect of methanol in comparison to other alcohols on the yield is not disclosed.

In companion patent applications, U.S. Pat. Nos. 4,052,420 and 4,052,437, the lower alcohols and phenols are indicated to be preferred for reacting nitrogen-containing compound and hydroxyl-containing compounds with carbon monoxide to obtain urethanes. The process disclosed in these references is catalyzed by a specific form of rhodium, i.e. amorphous rhodium oxide, and preferably requires either a two stage conversion (wherein the second stage is at a higher temperature and pressure than the first stage) or a nitrile-containing solvent. Methanol appears to increase selectivity to urethane at the higher temperature utilized in the second stage, but ethanol is preferred in the first stage. However, due to the unpredictability of catalysis this increase must be restricted to the specific catalyst and solvent utilized in the process disclosed. (Note that the patentee, at column 9, lines 8–15, of U.S. Pat. No. 4,052,420, indicates that it is not understood why ethanol is preferred in the first stage and methanol in the second stage of this process.)

Finally, British Pat. No. 1,089,132 teaches a rhodium catalyzed process for converting a nitrogen-containing organic compound and an alcohol to urethane in the presence of carbon monoxide, wherein methanol is said to be the preferred alcohol. However, the data in this patent indicates that n-butanol demonstrates increased selectivity to urethane as compared to methanol. (There is no data on ethanol provided, therefore one can not determine why methanol would be preferred over ethanol in the disclosed process.)

In the few references which suggest that ruthenium compounds are suitable catalysts for the carbonylation of nitrogen-containing organic compounds to the corresponding urethanes or isocyanates, the catalyst is either a ruthenium halide, or a halide-containing moiety is combined with the ruthenium compound to provide the active catalyst. For example, in U.S. Pat. Nos. 3,660,458; 4,134,880; 4,186,269; and 4,304,922 the ruthenium compound that has demonstrated catalytic activity is ruthenium chloride. (As noted above, in the latter three patents wherein urethanes are prepared, ethanol is disclosed as the preferred alcohol.) In U.S. Pat. Nos. 3,461,149 and 3,979,427 ruthenium-on-alumina is treated with halide-containing compounds, such as ferric chloride or 1,1,2-trichloro-1,2,2,-trifluoroethane, to provide a heterogeneous catalyst.

Another example of a heterogeneous ruthenium catalyst for the preparation of aromatic isocyanates may be found in U.S. Pat. No. 3,737,445. This patent discloses a gas-phase process for reacting carbon monoxide with an aromatic nitro or nitroso compound to yield an aromatic isocyanate.

Ruthenium compounds have been utilized in the reduction of organic nitro compounds to the corresponding amines with mixtures of hydrogen and carbon monoxide. It was reported in U.S. Pat. No. 3,729,512 that the reduction of the organic nitro compound with carbon monoxide and ethanol, in the absence of $H_2$, resulted in a mixture of amine and a urethane. The patentee was not concerned with the preparation of a urethane product; therefore, there was no attempt to increase the selectivity above the approximately 22 percent, urethane, that was obtained.

In the ruthenium-catalyzed processes described in above references, when an alcohol was included in the reaction mixtures, to yield a urethane reaction product, it was either ethanol (U.S. Pat. Nos. 4,186,269; 3,304,992; and 3,729,512) or isobutanol (U.S. Pat. No. 4,134,880).

SUMMARY OF THE INVENTION

It is, accordingly, one object of this invention to provide an improved process for converting a nitrogen-containing organic compound, selected from the group consisting of nitro, nitroso, azo and azoxy compounds into the corresponding urethane by reacting a solution, comprising methanol and a nitrogen-containing organic compound, with carbon monoxide, in the presence of a ruthenium-containing catalyst. In one embodiment of this invention, the improvement comprises increasing the rate of conversion of the nitrogen-containing organic compound and the selectivity of the conversion of said nitrogen-containing organic compound to the corresponding urethane by (a) providing a primary amine in the solution of methanol and the nitrogen-containing organic compound and (b) reacting the resulting solution with carbon monoxide in the presence of a halide-free ruthenium compound, at conditions sufficient to convert the nitrogen-containing organic compound to the corresponding urethane.

While not wishing to be bound by theory, it appears that, in the ruthenium catalyzed carbonylation of the above nitrogen-containing organic compound to the corresponding urethane, the nitrogen-containing organic compound must first be reduced to a primary amine which then undergoes oxidative carbonylation to the urethane. These reactions which are illustrated below (wherein [H] represents the ruthenium hydrogen carrier) must be effectively coupled to provide the desired selectivity to the urethane.

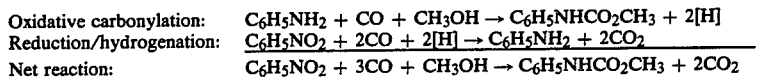

Thus the primary amine (illustrated by aniline) is an intermediate in the formation of urethane from the nitrogen-containing organic compound (illustrated by nitrobenzene). It has been found that the preferred halide-free ruthenium compounds used as catalysts in this invention are able to efficiently and rapidly reduce the nitrogen-containing organic compounds to the primary amine. The presence of iron chlorides or similar Lewis Acids is ineffective for increasing the activity of halide-free ruthenium catalysts.

In a carbonylation reaction wherein no primary amine is present, initially, the nitrogen-containing compound (e.g. nitrobenzene) can be reduced to the primary amine (aniline) by added hydrogen or hydrogen equivalents derived from water by the ruthenium-catalyzed water-gas shift reaction. It has been found that the reduction of the nitrogen-containing organic compound to a primary amine in the presence of hydrogen is rapid and provided that the molar ratio of hydrogen to the nitrogen-containing organic compound is less than 1, the remainder of the nitrogen-containing organic compound serves as the oxidant for the oxidative carbonylation of the primary amine to the urethane.

In the initial absence of primary amine, hydrogen or water, the hydrogen equivalents required to initially reduce nitrogen-containing organic compound to the primary amine are derived by dehydrogenation of the alcohol. (In the scheme illustrated below each R′ is independently selected from the group consisting of hydrogen and hydrocarbyl radical.)

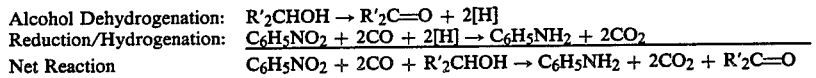

However, the carbonyl compounds which result for dehydrogenation of alcohol react with the primary amine to form undesired condensation products and water. Additional nitrogen-containing compound may then be reduced to the primary amine by hydrogen equivalents derived from water by the ruthenium catalyzed water gas shift reaction.

When sufficient primary amine is present in the reaction solution, either initially added or formed in situ by alcohol dehydrogenation, further alcohol dehydrogenation is undesired because it converts the nitrogen-containing organic compound to primary amine and higher products instead of urethane. It has been found that methanol is less susceptible to dehydrogenation to the aldehyde than ethanol and higher alcohols, in the presence of the ruthenium catalysts utilized in the process of the instant invention. Therefore the use of methanol improves the yield of urethane obtained in the final reaction product mixture and the combination of methanol and a primary amine in the process of the instant invention results in both an increased yield of urethane and an increased reaction rate.

The primary amine may also be provided by the in-situ decomposition of a urea or a biuret compound to the corresponding primary amine(s) and urethane in the reaction solution.

DETAILED DESCRIPTION OF THE INVENTION

The nitrogen-containing organic compound useful in the process of this invention will contain at least one non-cyclic group in which a nitrogen atom is directly attached to a single carbon atom and through a double bond to oxygen or another nitrogen atom. The nitrogen-containing organic compound is selected from the group consisting of nitro, nitroso, azo and azoxy compounds.

Examples of suitable nitrogen-containing organic compounds for use in the process of this invention are compounds represented by the general formulae:

$$R_1(NO_x)_y \quad \quad \text{I}$$

and $$R_1-N=N(O)_z-R_2 \quad \quad \text{II}$$

wherein $R_1$ and $R_2$ are radicals independently selected from the group consisting of $C_1$ to $C_{20}$ hydrocarbyl radicals and substituted derivatives thereof, x is an integer of from 1 to 2, y is an integer of from 1 to 3, and z is an integer of from 0 to 1. The substituted hydrocarbyl radical may include hetero atoms selected from the group consisting of halogen, oxygen, sulfur, nitrogen and phosphorous atoms.

The nitrogen-containing compounds represented by formula I include nitro compounds (wherein x is 2) and nitroso compounds (wherein x is 1). Suitable nitro compounds are mononitro compounds such as nitrobenzene, alkyl and alkoxy nitrobenzenes wherein the alkyl group contains up to 10 carbon atoms, aryl and aryloxy nitrobenzenes, wherein the aryl group is phenyl, tolyl, naphthyl, xylyl, chlorophenyl, chloronitrobenzenes, aminonitrobenzenes, carboalkoxyamino nitrobenzenes wherein the alkoxy group has up to 10 carbon atoms, aryl and aryloxy dinitrobenzenes, trinitro compounds such as trinitrobenzene, alkyl and alkoxytrinitrobenzenes, aryl and aryloxytrinitrobenzenes, the substituents being any of those already mentioned and chlorotrinitrobenzenes as well as similarly substituted mono and polynitro derivatives of the naphthalene, diphenyl, diphenylmethane, anthracene and phenanthrene series. Substituted or unsubstituted aliphatic nitro compounds such as nitromethane, nitrobutane, 2,2'-dimethyl nitrobutane, nitrocyclopentane, 3-methylnitrobutane, nitrooctadecane, 3-nitropropene-1, phenyl nitromethane, p-bromophenyl nitromethane, p-methoxy phenyl nitromethane, dinitroethane, dinitrohexane, dinitrocyclohexane, di-(nitrocyclohexyl)-methane are also suitable. The above nitro compounds may include more than one of the above substitutents (in addition to the nitro group (s) such as in nitroaminoalkylbenzenes, nitroalkylcarboalkoxyamino benzenes, etc. From this group of nitro compounds nitrobenzene, nitrotoluene, dinitrobenzene, dinitrotoluene, trinitrobenzene, trinitrotoluene, mononitronaphthalene, dinitronaphthalene, 4,4'-dinitrodiphenylmethane, nitrobutane, nitrocyclohexane, p-nitrophenylnitromethane, dinitrocyclohexane, dinitromethylcyclohexane, dinitrocyclohexylmethane, nitroaminotoluene and nitrocarboalkoxyaminotoluene are preferred and in particular aromatic nitro compounds especially 2,4-and 2,6-dinitrotoluenes, meta and para dinitrobenzenes, and 5-nitro-2-methyl-carboalkoxyamino-, 2-nitro-5-methyl-carboalkoxyamino-, and 3-nitro-2-methyl-carboalkoxyamino benzenes.

Examples of suitable nitroso compounds are the aromatic nitroso compounds such as nitrosobenzene, nitrosotoluene, dinitrosobenzene, dinitrosotoluene and the aliphatic nitroso compounds such as nitrosobutane, nitrosocyclohexane and dinitrosomethylcyclohexane.

The nitrogen-containing compounds represented by Formula II include both azo compounds (wherein z is 0) and azoxy compounds (wherein z is 1). Suitable compounds represented by formula II include azobenzene, nitroazobenzene, chloroazobenzene, alkyl or aryl substituted azobenzene, azoxybenzene, nitroazoxybenzene, chloroazoxybenzene, etc.

The process of this invention includes the use of any mixture of nitro compounds, nitroso compounds, azo or azoxy compounds with any mixture of hydroxy compounds and also the use of compounds containing both functions, i.e. hydroxynitro compounds, hydroxynitroso compounds, hydroxyazo and hydroxyazoxy compounds such as 2-hydroxynitroethane, 2-hydroxynitrosoethane, nitrophenols, nitronaphthols, nitrosophenols, nitrosonaphthols, hydroxyazobenzenes and hydroxyazoxybenzenes. Mixtures of these nitrogen-containing compounds may also be used.

This process of the invention has been found to proceed most smoothly to give the highest yields when employing nitro compounds. It is accordingly preferred to use nitro compounds rather than nitroso, azo or azoxy compounds.

The primary amine compound utilized in the process of this invention may be selected from the group consisitng of compounds represented by the general formula:

$$R_1(NH_2)_y \quad \quad \text{IV}$$

wherein $R_1$ and Y are as defined above. Examples of such primary amines include methylamine, ethylamine, butylamine, hexylamine, ethylenediamine, propylenediamine, butylenediamine, cyclohexylamine, cyclohexyldiamine, aniline, p-toluidine, o-, m- and p-diaminobenzenes, amino-methylcarbanilic acid esters, especially the 5-amino-2 methyl-, 2-amino-5-methyl-, and 3-amino-2-methyl carboalkoxyaminobenzenes, wherein said alkoxy group has up to 10 carbon atoms, o-, m- and p-nitroanilines, nitroaminotoluenes, especially those designated above, o- and p-phenylenediamine, benzylamine, o-amino-p-xylene, 1-aminophthaline, 2,4- and 2,6-diaminotoluenes, 4,4'-diaminodibenzyl, bis (4-aminophenyl) thioether, bis (4-aminophenyl) sulfone, 2,4,6-triaminotoluene, o-, m- and p-chloranilines, p-bromoaniline, 1-fluoro-2,4-diaminobenzene, 2,-4-diaminophenetole, o,-m- and p-aminoanisoles, ethyl p-aminobenzoate, 3-aminophthalic anhydride, etc. These amino compounds may be used alone or in combination.

Among the above-enumerated amino compounds, those which can be derived from the starting nitro compound are preferred. For example, when nitrobenzene is used as the starting aromatic nitro compound, aniline is preferred. Similarly, 2-amino-4-nitrotoluene, 4-amino-2-nitrotoluene, and 2,4-diaminotoluene are preferably used when the starting aromatic nitro compound is 2,4-dinitrotoluene, while 2-amino-6-nitrotoluene, and 2,6-diaminotoluene are preferably used when the starting aromatic nitro compound is 2,6-dinitrotoluene.

The primary amine compound can be provided by the in-situ decomposition of the corresponding urea or biuret as represented by compounds having the general formulae:

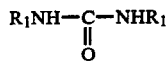

and

respectively, wherein $R_1$ is as defined above. Of course, since the above urea and biuret will comprise more than one radical, $R_1$ may represent different radicals in the same compound. That is non-symmetrical ureas and biurets, e.g.

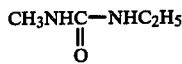

are within the scope of the invention.

The catalyst utilized in the process of this invention preferably comprises a halide-free ruthenium compound. Unlike other platinum group metal-containing catalysts for the carbonylation of nitrogen-containing organic compounds, the presence of halide in ruthenium catalysts, either as the anion of a ruthenium salt or in a Lewis acid decreases the activity of the ruthenium catalyst. Thus, although $RuCl_3$ and the like may be utilized in the instant process, the ruthenium compound is preferably selected from ruthenium salts, such the nitrate, sulfate, acetate, formate, carbonate, etc. and ruthenium complexes (especially ruthenium carbonyl complexes) including ligands capable of coordinating with the ruthenium atom. The complex may include one or more ruthenium atoms and suitable ligands may include carbon-carbon unsaturated groups as in ethylene, isobutylene, cyclohexene, cyclopentadiene, norbornadiene, cyclooctatetraene. Other suitable ligands include acetylacetonate (acac), hydrogen atoms, carbon monoxide, nitric oxide, alkyl-radicals, alkyl or aryl nitriles or isonitriles, nitrogen-containing heterocyclic compounds such as pyridine, 2,2′-bipyridine (bipy), piperidine, and organo phosphines, arsines or stibines.

The ruthenium catalyst is preferably utilized as a homogeneous catalyst and therefore one criteria for the selection of the ruthenium compound is its solubility under the conditions of reaction in the mixture of the nitrogen-containing organic compound, methanol and the primary amino compound (if included). The ruthenium compound is also selected with a view toward the catalytic activity of the compound. Thus the organo phosphines and the carbonyls are useful ligands for incorporation into the ruthenium catalyst utilized in the process of the instant invention.

Suitable organophosphines include compounds represented by the following formula $$(R_3)(R_4)P(R_5) \qquad V$$

wherein $R_3$, $R_4$ and $R_5$ are radicals independently selected from the group consisting of hydrogen, hydrocarbyl, and substituted derivatives of hydrocarbyl radicals, and wherein the substituted hydrocarbyl radicals may include heteroatoms selected from the group consisting of halogen, oxygen, sulfur, nitrogen and phosphorous atoms. Preferably the above hydrocarbyl radicals will comprise from 1 to about 20 atoms, e.g. from about 1 to about 10 carbon atoms. Suitable radicals include methyl, ethyl, n-propyl, isopropyl, butyl, 2-chlorobutyl, n-propoxy, 2-nitro pentyl, phenyl, fluorophenyl, o, m, and p-methylphenyl, etc.

Examples of suitable organophosphines include triphenylphosphine, methyldiphenylphosphine, tris o-chlorophenylphosphine, tri-n-propylphosphine, tris-p-methoxybenzylphosphine, etc.

Other useful organophosphines ligands include chelating bisphosphines. Thus at least one of the radicals, $R_3$, $R_4$ or $R_5$ will include a hetero-phosphorous atom that (along with the phosphorous atom of Formula V) is capable of coordinating with the ruthenium atom. Such chelating bisphosphines may be represented by the general formula $$(R_3)(R_4)P(R_6)P(R_3)(R_4) \qquad VI$$

wherein $R_3$ and $R_4$ are as defined above and $R_6$ is a divalent radical providing sufficient spacing to enable both phosphorous atoms to coordinate with the ruthenium atom. $R_6$ may be a hydrocarbyl radical having from 2 to 10 carbon atoms or a substituted derivative thereof including one or more heteroatoms selected from the group consisting of halogen, oxygen, sulfur, nitrogen and phosphorous atoms. Preferably, $R_6$ comprises from 2 to 6 carbon atoms.

Examples of suitable bis phosphines include:
bis(1,2-diphenylphosphino)benzene
bis(1,3-diphenylphosphino)propane
bis(1,2-diphenylphosphino)ethane A bisphosphino ruthenium catalyst compound may be preformed or formed in-situ in the reaction solution by separately dissolving a bisphosphino-free ruthenium compound and a bisphosphine. If a bisphosphino ligand is to be included in the catalysts, preferably the bisphosphino ruthenium compound is preformed to ensure that the bisphosphino ligand will be coordinated to the ruthenium atom during the reaction.

Examples of halide-free ruthenium compounds which are suitable as catalysts for the process of this invention include:
$Ru_3(CO)_{12}$
$H_4Ru_4(CO)_{12}$
Ruthenium acetylacetonate
$Ru_3(CO)_9[P(C_6H_5)_3]_3$
[bis(1,2-diphenylphosphino)benzene]ruthenium tricarbonyl
[bis(1,2-diphenylphosphino)ethane]ruthenium tricarbonyl
[bis(1,3-diphenylphosphino)propane]ruthenium tricarbonyl When a primary amine is utilized in the instant process, no particular limitation is placed on the amount of primary amine used. However, it is preferably used in an amount equal to from 0.1 to 100 moles per gm-atom of nitrogen in the nitrogen-containing organic compound.

The process of the invention may be carried out in the absence of solvent but the use of a solvent is not precluded. Suitable solvents include, for example, aromatic solvents such as benzene, toluene, xylene, etc.; nitriles such as acetonitrile, benzonitrile, etc.; sulfones such as sulfolane, etc.; halogenated aliphatic hydrocarbons such as 1,1,2-trichloro-1,2,2,-trifluoroethane, etc.; halogenated aromatic hydrocarbons such as monochlorobenzene, dichlorobenzene, trichlorobenzene, etc.; ketones; esters; and other solvents such as tetrahydrofuran, 1,4-dioxane, 1,2-dimethoxyethane, etc.

In carrying out the process of the invention, the methanol and carbon monoxide may be used in amounts equal to at least 1 mole per gm-atom of nitrogen in the nitrogen-containing compound. Preferably, methanol is used in excess and functions as a solvent as well as reactant.

The amount of the ruthenium compound used as the catalyst may vary widely according to the type thereof and other reaction conditions. However, on a weight basis, the amount of catalyst is generally in the range of from $1 \times 10^{-5}$ to 1 part, and preferably from $1 \times 10^{-4}$ to $5 \times 10^{-1}$ parts, per gram-atom of nitrogen in the starting nitrogen-containing organic compound when expressed in terms of its metallic component.

The reaction temperature is generally held in the range of 80° to 230° C., and preferably in the range of from 130° to 200° C.

The reaction pressure, or the initial carbon monoxide pressure, is generally in the range of from 10 to 1,000 kg/cm$^2$G, and preferably from 30 to 500 kg/cm$^2$G.

The reaction time depends on the nature and amount of the nitrogen-containing organic compound used, the reaction temperature, the reaction pressure, the type and amount of catalyst used, the type of reactor employed, and the like, but is generally in the range of from 5 minutes to 6 hours. After completion of the reaction, the reaction mixture is cooled and the gas is discharged from the reactor. Then, the reaction mixture is subjected to any conventional procedure including filtration, distillation, or other suitable separation steps, whereby the resulting urethane is separated from any unreacted materials, any by-products, the solvent, the catalyst, and the like.

The urethanes prepared by the process of the invention have wide applications in the manufacture of agricultural chemicals, isocyanates, and polyurethanes.

This invention is more fully illustrated by the following examples. However, they are not to be construed to limit the scope of the invention.

In each of the following examples, the reaction was conducted in batch mode in a 300 ml stainless steel autoclave reactor equipped with a stirring mechanism which provides constant dispersion of the gas through the liquid solution. Heating of the reaction is provided by a jacket-type furnace controlled by a proportioning controller. The autoclave is equipped with a high pressure sampling system for removal of small samples of the reaction solution in order to monitor the reaction progress. Reaction samples were analyzed by gas chromatography.

EXAMPLE 1

75 ml of a solution containing 12.31 g (0.100 mole) nitrobenzene and 2.68 g t-butylbenzene (internal standard for gas chromatographic analyses) in methanol and 0.128 g (0.211 millimole) Ru$_3$(CO)$_{12}$ were placed in the reactor vessel. The gas in the vessel was replaced with carbon monoxide and pressurized with carbon monoxide to 1000 p.s.i.g. at ambient temperature. The reactor contents were then heated to 160° C. Complete conversion of the nitrobenzene occurred in 26 hours at 160° C. and yielded 0.038 mole methyl N-phenylcarbamate, 0.032 mole aniline, 0.009 mole formylidene aniline, and 0.003 mole N-methyl aniline. The balance (0.018 mole) was converted to higher molecular weight products derived from aniline.

COMPARATIVE EXAMPLE 1

The procedure was the same as for Example 1 with the exception that ethanol was substituted for methanol on an equal volume basis. Complete conversion of the nitrobenzene occurred in 4.5 hours at 160° C. and yielded 0.007 mole ethyl N-phenylcarbamate, 0.066 mole aniline, 0.004 mole ethylidene aniline, and 0.002 mole N-ethyl aniline. The balance (0.021 mole) was converted to higher molecular weight products derived from aniline.

It is thus clear that the selectivity of the ruthenium catalyzed conversion of nitrobenzene to an alkyl N-phenylcarbamate is higher for the syntheses of methyl N-phenylcarbamate using methanol than for the syntheses of ethyl N-phenylcarbamate using ethanol. It will be appreciated by those skilled in the art that both carbamates may be decomposed to yield the desired isocyanate compound.

EXAMPLE 2

The procedure was the same as for Example 1 with the exception that 4.66 g (0.050 mole) aniline was added before the reaction. The volume of methanol was correspondingly reduced so that the total solution volume was 75 ml. Complete conversion of the nitrobenzene occurred in 8.5 hours at 160° C. and yielded 0.076 mole methyl N-phenylcarbamate, and 0.017 mole additional aniline (0.067 mole total aniline).

COMPARATIVE EXAMPLE 2

The procedure was the same as for Example 2 with the exception that ethanol was substituted for methanol on an equal volume basis. Complete conversion of the nitrobenzene occurred in 4.5 hours at 160° C. and yielded 0.014 mole ethyl N-phenylcarbamate, and 0.058 mole additional aniline (0.108 mole total aniline). The balance (0.023 mole) appeared as by-products derived from aniline. It is thus clear that the selectivity of the ruthenium catalyzed conversion of nitrobenzene and methanol to methyl N-phenylcarbamate is higher than the selectivity of the corresponding conversion of nitrobenzene and ethanol to ethyl N-phenylcarbamate even when aniline is added in order to improve the selectivity.

EXAMPLE 3

The procedure was the same as for Example 2 with the exception that 0.127 g (0.201 mole)(bis(1,2-diphenylphosphino) benzene) ruthenium tricarbonyl was used as the ruthenium catalyst precursor. Complete conversion of the nitrobenzene occurred in 11.5 hours at 160° C. and yielded 0.074 mole methyl N-phenylcarbamate and 0.010 mole additional aniline (0.060 mole total aniline).

COMPARATIVE EXAMPLE 3

The procedure was the same as for Example 3 with the exception that ethanol was substituted for methanol on an equal volume basis. Complete conversion of the nitrobenzene occurred in 21 hours at 160° C. and yielded 0.017 mole ethyl N-phenylurethane and 0.052 mole additional aniline (0.102 mole total aniline).

While particular embodiments of the invention have been described, it will be understood, of course, that the invention is not limited thereto since many obvious modifications can be made and it is intended to include within this invention any such modifications as will fall within the scope of the appended claims.

Having now described the invention, what is claimed is:

1. A process for converting a nitrogen-containing organic compound, selected from the group consisting of nitro, nitroso, azo, and azoxy compounds, into the corresponding urethane, by reacting a solution comprising said nitrogen-containing organic compound and methanol with carbon monoxide, which comprises contacting said solution with carbon monoxide, in the presence of a catalyst comprising ruthenium at conditions sufficient to convert said nitrogen-containing organic compound into the said corresponding urethane.

2. The process of claim 1 wherein said nitrogen containing organic compound is a nitro compound.

3. The process of claim 2 wherein said nitro compound is an aromatic nitro compound.

4. The process of claim 3 wherein said catalyst comprises a halide-free ruthenium compound.

5. The process of claim 4 wherein said catalyst comprises a ruthenium compound including a phosphine ligand.

6. The process of claim 3 wherein said aromatic nitro-compound is selected from the group consisting of nitrobenzene, nitroanisole, dinitrotoluene, dinitrobenzene, nitromesitylene, bis(4-nitrophenyl) methane, nitroaminotoluene and nitrocarboalkoxyaminotoluene.

7. A process for converting a nitro-containing organic compound into the corresponding urethane, by reacting a solution comprising said nitro-containing organic compound and methanol with carbon monoxide, which comprises contacting said solution with carbon monoxide, in the presence of a catalyst comprising a halide-free ruthenium compound at conditions sufficient to convert said nitro-containing organic compound into the said corresponding urethane.

8. The process of claim 7 wherein said nitro compound is an aromatic nitro compound.

9. The process of claim 8 wherein said aromatic nitro-compound is selected from the group consisting of nitrobenzene, nitroanisole, dinitrotoluene, nitromesitylene, bis(4-nitro-phenyl) methane, nitroaminotoluene and nitrocarboalkoxyaminotoluene.

10. The process of claim 8 wherein said halide-free ruthenium compound comprises a phosphine ligand.

11. The process of claim 10 wherein said phosphine ligand is bisphosphine ligand.

12. A process for converting a nitro-containing organic compound into the corresponding urethane, by reacting a solution comprising said nitro-containing organic compound and methanol with carbon monoxide, which comprises the steps of:
(a) providing a primary amine in said solution,
(b) contacting the solution of step (a) with carbon monoxide, in the presence of a catalyst comprising ruthenium at conditions sufficient to convert said nitrogen-containing organic compound into the said corresponding urethane.

13. The process of claim 12 wherein said nitro-containing organic compound is an aromatic nitro compound and said primary amine is the corresponding aromatic amine.

14. The process of claim 13 wherein said primary amine is provided by reduction of said nitro-containing compound with hydrogen in said solution.

15. The process of claim 13 wherein said primary amine is provided by reduction of said nitro-containing compound with hydrogen equivalents derived from the ruthenium-catalyzed water-gas shift reaction.

16. The process of claim 13 wherein said amine is provided by decomposing a urea or biuret in-situ.

17. The process of claim 13 wherein said catalyst comprises a halide-free ruthenium compound.

18. The process of claim 17 wherein said halide-free ruthenium compound comprises a phosphine ligand.

19. The process of claim 17 wherein said aromatic nitro-compound is selected from the group consisting of nitrobenzene, nitroanisole, dinitrotoluene, dinitrobenzene, nitromesitylene, bis(4-nitrophenyl) methane, nitroaminotoluene and nitrocarboalkoxyaminotoluene.

20. A process for converting a nitro-containing organic compound into the corresponding urethane, by reacting a solution comprising said nitro-containing organic compound and methanol with carbon monoxide, which comprises the steps of:
(a) providing a primary amine in said solution,
(b) contacting the solution of step (a) with carbon monoxide, in the presence of a catalyst comprising a halide-free ruthenium compound, at a temperature of at least about 130° C. and a carbon monoxide pressure of at least about 200 psig to convert said nitro-containing organic compound to said corresponding urethane, and
(c) recovering said urethane.

21. The process of claim 20 wherein said nitro-containing organic compound is an aromatic nitrocompound and said primary amine is the corresponding aromatic amine.

22. The process of claim 21 wherein said aromatic nitro compound is selected from the group consisting of nitrobenzene, nitroanisole, dinitrotoluene, dinitrobenzene, nitromesitylene, bis(4-nitrophenyl)methane, nitroaminotoluene and nitrocarboalkoxyaminotoluene.

23. The process of claim 22 wherein said nitro-containing organic compound is nitrobenzene and said primary amine is aniline.

24. The process of claim 21 wherein said halide-free ruthenium compound comprises a phosphine ligand.

25. The process of claim 24 wherein said phosphine ligand is a bisphosphine ligand.

26. The process of claim 25 wherein said phosphine ligand is bis(1,2-diphenylphosphino)benzene.

* * * * *